United States Patent [19]
Zia et al.

[11] Patent Number: 6,090,368
[45] Date of Patent: Jul. 18, 2000

[54] PHARMACEUTICAL COMPOSITIONS FOR INTRANASAL SPRAY ADMINISTRATION OF KETOROLAC TROMETHAMINE

[75] Inventors: Hossein Zia; Thomas E. Needham, both of Wakefield; Muhammad Quadir, Kingston, all of R.I.

[73] Assignee: The Board of Governors for Higher Education, State of Rhode Island and Providence Plantations, Providence, R.I.

[21] Appl. No.: 09/033,994

[22] Filed: Mar. 3, 1998

[51] Int. Cl.$^7$ ...................................................... A61L 9/14
[52] U.S. Cl. ........................... 424/45; 424/434; 424/484; 424/485; 424/487; 424/488; 424/489; 424/491; 514/958
[58] Field of Search ..................................... 424/434, 484, 424/485, 487, 488, 489, 491, 45; 514/75, 958, 772.4, 772.6, 774, 775, 776, 777, 778, 780, 781

[56] References Cited

U.S. PATENT DOCUMENTS 5,639,738  6/1997  Falk et al. .................................. 514/54
5,736,161  4/1998  Garces et al. ............................ 424/493

OTHER PUBLICATIONS

Santus et al. Nasal formulations of ketorolac tromethamine–technological evaluation—bioavailability and tolerabil;ity in rabbits. FARMCO. vol. 48(12). pp. 1709–1723, 1993.

Dondeti et al. Biadhesive and formulation parameters affecting nasal absorption. International Journal of Pharmaceuticlas. vol. 126. 115–133, 1996.

Santus et al. Nasal Formulations of ketorolac tromethamine–technological evaluation—bioavailability and tolerability in rabbits. FARMCO, vol. 48 (12). pp. 1709–1723, 1993.

Dondeti etal. Bioadhesive and formulation parameters affecting nasal absorption. International Journal of Pharmaceutics. vol. 126. 115–133, 1996.

The influence of tonicity and viscosity on the intranasal absorption of salmon calcitonin in rabbits, Ramneik Dua et al., International Journal of Pharmaceutics, 174 (1997) 233–242.

Bioadhesive and formulation parameters affecting nasal absorption, Polireddy Dondeti et al., International Journal of Pharmaceutics, 127 (1996) 115–133.

In vivo evaluation of spray formulations of human insulin for nasal delivery, Polireddy Dondeti et al., International Journal of Pharmaceutics, 122 (1995) 91–105.

Ketorolac as a rapid and effective treatment of migraine headache: evaluations by patients, Charles P. Davis, et al., American Journal of Emergency Medicine, vol. 11, No. 6, Nov. 1993, 573–575.

Ketorolac in acute headache management, R. Norman Harden, et al., Headache, 31:463–464, 1991.

Self–administration of parenteral ketorolac tromethamine for head pain, L. Jay TurkeWitz et al., Headache, 1992; 32: 452–454.

Recent advances in the acute management of migraine and cluster headaches, Kusum L. Kumar, Clinical Review, 339–348, 1994.

Ketorolac tromethamine in cancer pain, Suayib Yalcin et al., Acta Oncologica, vol. 36, No. 2, pp. 231–232, 1997.

(List continued on next page.)

*Primary Examiner*—Thurman K. Page
*Assistant Examiner*—Lakshmi Channavajjala
*Attorney, Agent, or Firm*—Samuels, Gauthier & Stevens

[57] ABSTRACT

A pharmaceutical composition of a water soluble drug admixed with an aqueous bioadhesive cellulosic polymer containing microcrystalline particles. When sprayed (via a conventional spray device) into the nose, drug molecules are retained in contact with the nasal membrane. The drug composition comprises ketorolac tromethamine in an aqueous nasal polymeric spray formulation that without the addition of any permeation enhancer will promote drug absorption and provides absolute drug bioavailability greater than 90%.

4 Claims, 4 Drawing Sheets

OTHER PUBLICATIONS

Recommendations for the emergency treatment of migraine headache, Bob L. Lobo et al., Feb., 1994, 53–54.

The use of ketorolac in the management of postoperative pain, J. Robin DeAndrade, et al., Review, vol. 17, No. 2, Feb 1994, 157–166.

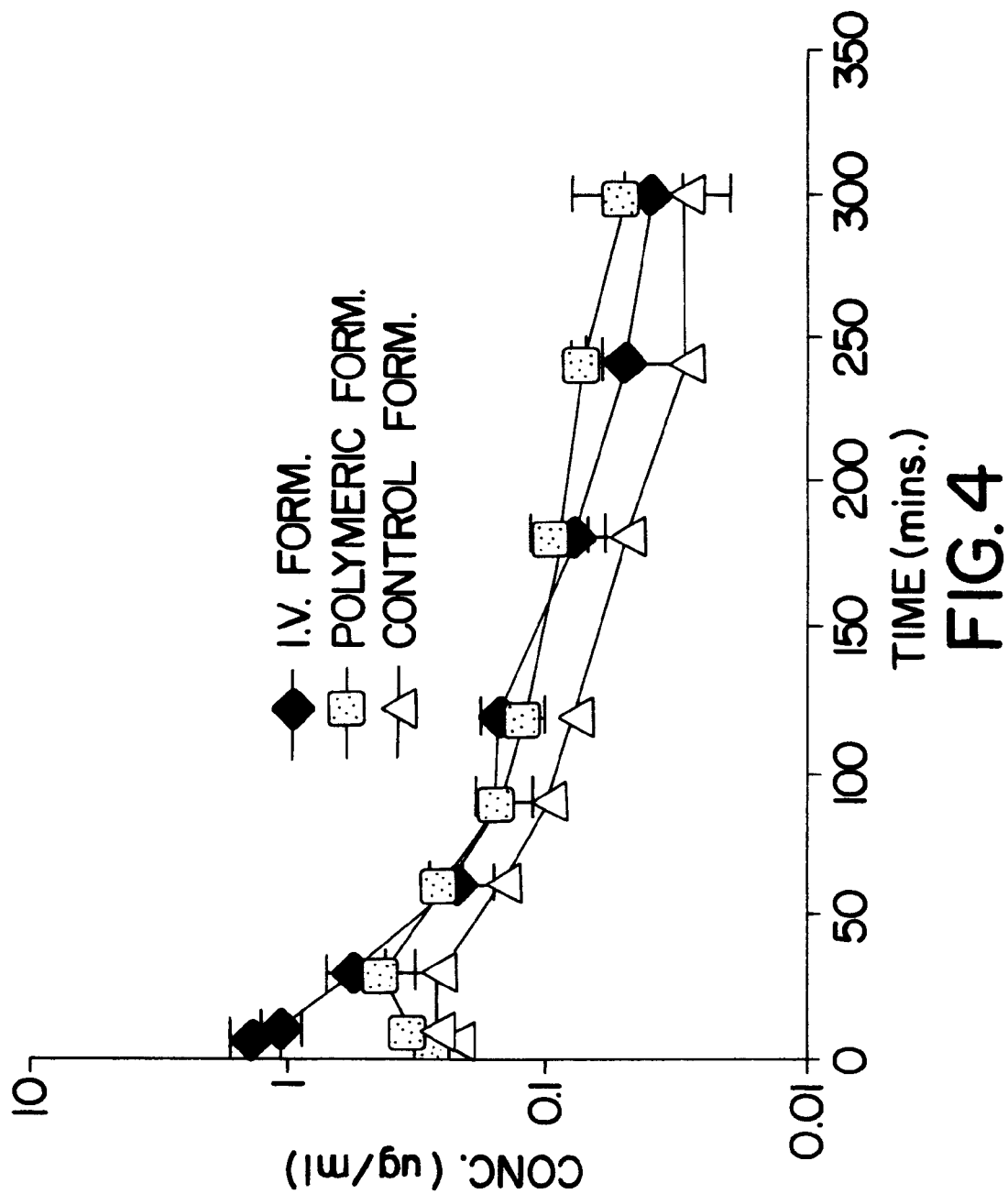

PHARMACEUTICAL COMPOSITIONS FOR INTRANASAL SPRAY ADMINISTRATION OF KETOROLAC TROMETHAMINE

BACKGROUND OF THE INVENTION

1. Field of the Invention

A pharmaceutical nasal spray formulation of ketorolac tromethamine for the treatment of pain such as caused by postoperative pain, cancer pain and migraine headache. When administered intranasally to a mammal, the necessary blood level of the drug is provided to effectively treat the pain.

2. Description of Related Art

The intranasal route of administration provides an effective and convenient means of drug delivery, especially when the most popular route, the oral route, is inappropriate and/or ineffective. The nasal route offers some advantages such as by-passing the metabolic limitation pathways of gastrointestinal tract and liver, thereby significantly increasing the effectiveness of the drug. The nasal mucosa offers a large surface area and relatively low enzymatic degradation resulting in a rapid absorption of drugs into the systemic circulation producing high plasma levels similar to those provided by injections. While parenteral administration also bypasses the gastrointestinal tract and delivers the drug formulations directly into the bloodstream and the surrounding tissues of the recipient, it has several disadvantages such as pain of injection, inconvenience and thus poor patient compliance. In past several years, the effectiveness of this route for delivery of certain drugs such as insulin, calcitonin and testosterone has been documented, Dondeti, P.; Zia, H.; and Needham, *In Vivo Evaluation of Spray Formulations of Human Insulin for Nasal Delivery*, Int. J. Pharm. 122, 91 (1995); Dondeti, P.; Zia, H.; and Needham, E. E., *Bioadhesive and Formulation Parameters Affecting Nasal Absorption,* Int. J. Pharm., 127, 115 (1996); Dua, R.; Zia, H.; and Needham, T. E., *The Influence of Tonicity and Viscosity on the Intranasal Absorption of Salmon Calcitonin in Rabbits,* Int. J. Pharm., 147, 233 (1997); and Ko, K. T.; Zia, H.; Needham, T. E.; *Testosterone Emulsion Formulations of Nasal Administration,* J. of Microencapsulation, Accepted Nov. 10, 1996.

Ketorolac tromethamine is a highly potent non-narcotic analgesic with a moderate anti-inflammatory activity. It is efficacious in treating pain arising from a broad spectrum of causes, such as postoperative pain, cancer pain, migraine headache and pain from dental extractions, Suayib, Y.; Ibrahim, G.; Gulten, T.; Cermil, S.; *Ketorolac Tromethamine in Cancer Pain,* Acta Oncologica 36 231–232, (1997); and DeAndrade, R. J.; Maslanka, M.; *The Use of Ketrolac in the Management of Postoperative Pain,* Orthopedics, 17, 157–166, (1994). Several recent studies have examined the use of ketorolac in the emergency treatment of migraine headache via injections. An intramuscular injection of 60 mg dose of ketorolac was found to be as effective as meperidine and hydroxyzine in treating migraine headaches. It provided a significant reduction of symptoms in approximately 30 minutes to 1 hour after intramuscular administration and lasted for 6 hours. The emergency management of migraine headache is based on rest and the administration of anti-emetics and analgesics. The use of dihydroergotamine (DHE) in the emergency department is limited because of its side effects including vomiting. The problems facing the emergency physicians when treating migraine, include narcotic abuse and the liability of releasing patients who had received central nervous depressants. Ketorolac has less adverse side effects than narcotic drugs, does not have the side effects associated with DHE and has not been shown to have physiological addictive potential, this drug appears to be an excellent choice for treating migraine headache.

SUMMARY OF THE INVENTION

The present invention provides a pharmaceutical nasal spray composition containing ketorolac tromethamine that provides a therapeutic blood level comparable to that of its injection. In particular, the present invention alleviates many of the problems associated with the present treatment of pain, especially in the case of migraine headache.

Ketorolac tromethamine is carried in a fluid medium which is especially formulated to transport the drug for intranasal administration. Preferably, ketorolac tromethamine is admixed with polymeric bioadhesives selected from the group consisting of cellulosic materials, polyacrylics, gums, cyclodextrins, chitosans, hyaluronates, albumins and phosphlipids.

Although the preferred embodiment will be described in reference to ketorolac tromethamine, it is believed that other drugs suitable for purposes of the invention including other non-narcotic analgesic and anti-inflammatory drugs as well as other salts/complexes or free acid.

BRIEF DESCRIPTION OF THE DRAWINGS

FIG. 4 shows the comparative bioavailability various formulations.

DESCRIPTION OF THE PREFERRED EMBODIMENT(S)

Figure 1:
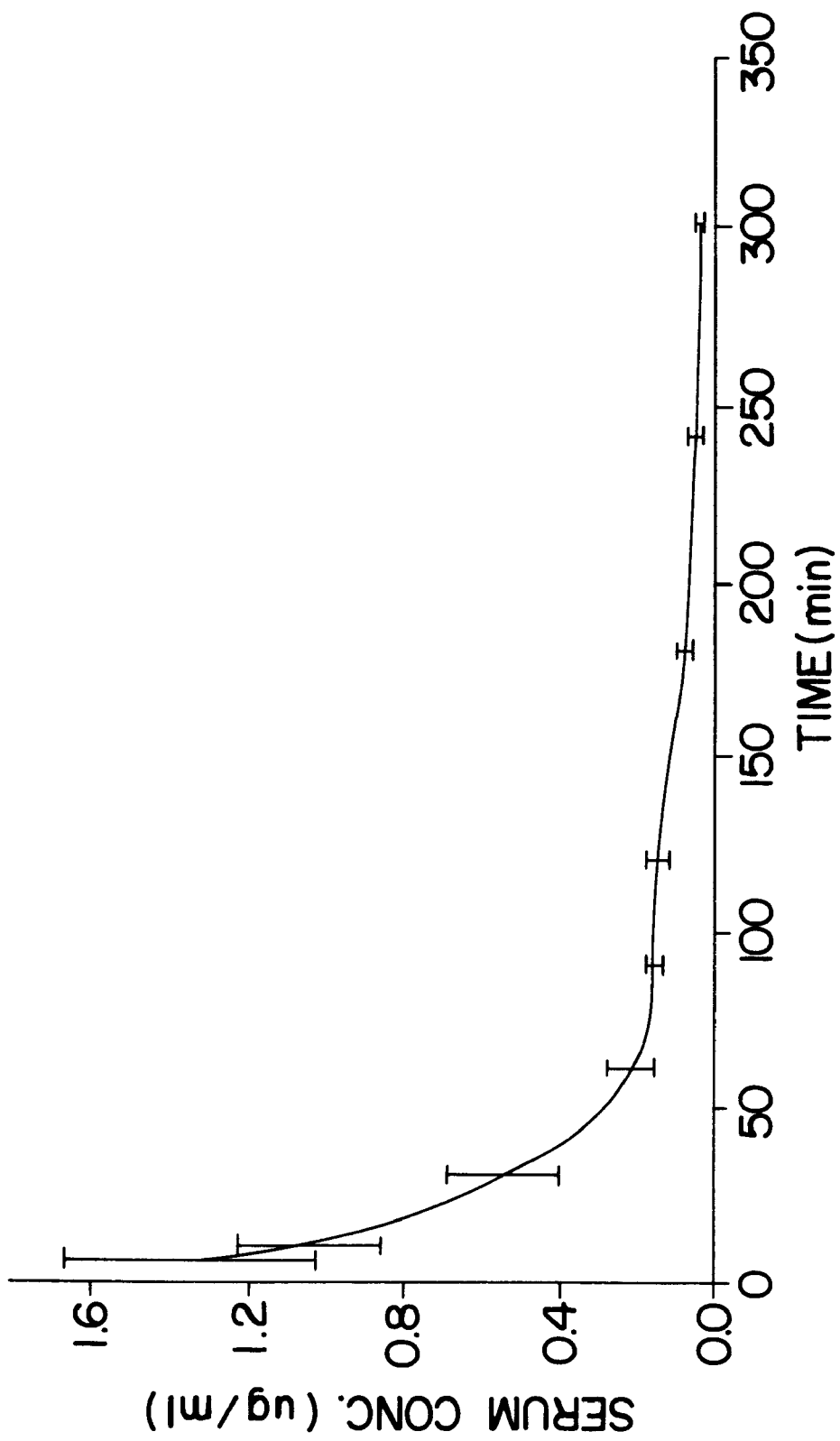
FIG. 1 shows the blood profile of ketorolac following an intravenous injection of drug (10 mg/mL of normal saline) in rabbits.

The invention will be described with reference to the following non-limiting Examples.

EXAMPLE I

Preparation of Formulation 1.5 gm of a polymeric bioadhesive, microcrystalline cellulose, Avicel®, FMC Corporation was dispersed in 70 ml of distilled water and mixed at 500–2000 rpm, preferably at 1500 rpm for 1–2.5 hours, preferably for 2 hours to be hydrated. 0.1 ml of Tween 80 was subsequently added and mixed for 2 minutes. 4.1 gms of dextrose was added slowly to this solution to adjust its tonicity. Then, 0.25–0.5 preferably 0.25 ml of 2-phenyl ethyl alcohol was added as a preservative and anti-caking agent and the formulation was mixed for 30 minutes until it was completely hydrated and homogeneous forming a colloidal microcrystalline cellulose suspension. Five grams ketorolac tromethamine was dissolved separately in 20 ml of distilled water and added slowly to the colloidal microcrystalline cellulose suspension. The volume was adjusted with distilled water to 100 ml and formulation was mixed for another 30 minutes. The pH of the formulation of was adjusted with HCl or NaOH to 5.8–6.1.

A control solution of the drug was prepared by dissolving 5 gm of ketorolac tromethamine and 4.1 gm of dextrose in a total 100 ml of distilled water. The pH of the formulation was 6.1

EXAMPLE II

Comparison of Nasal and Intravenous Administration of Ketorolac Tromethamine in Rabbits This study investigated the bioavailability of ketorolac tromethamine following the intranasal administration of essentially the same formulation described in Example I. The study protocol was approved by the Institutional Animal Care and Use Committee, University of Rhode Island, Kingston, R.I.

The animals used in this study were male New Zealand white rabbits weighing approximately 4–5 Kg (Charles River Labs, Amherst, Mass.). The animals were housed individually in cages and given standard animal chow and water. All animals were treated according to the guiding principles for laboratory Animal Care of the American Physiological Society. Throughout the experiment each rabbit was fasted for 12 hours prior to the experiment with free access to water. Rabbits were chosen randomly and a wash out period fo 2 weeks was allowed between each treatment. Each rabbit received 5 mg/kg of acepromazine maleate intramuscularly as a preanesthetic followed by 50 mg/kg of ketamine hydrochloride and 8.9 mg/kg of xylazine as a combined does for anesthetic purposes. A catheter was placed in the rabbit's ear artery to allow withdrawal of multiple blood samples throughout the experiment. The ketorolac formulations were administered either by the intravenous or intranasal route. The intravenous dose was prepared as 2 mg/kg of the rabbit's weight in 0.9% NaCl solution. 5 mg/100 $\mu$l does of nasal formulation were delivered via a spray pump with one spray in each nostril. Blood samples (0.8–1.0 ml) were collected at 5, 10, 30, 60, 90, 120, 180, 240 and 300 minutes after administration. All blood samples were placed into plasma supernatory separated tubes and centrifuged at 3000 rpm for 12 minutes within 20–30 minutes after collection in order to obtain the serum. The supernatant serum samples were transferred into tubes, sealed and stored at −70° C. until assayed.

The extraction of ketorolac tromethamine from the serum was carried out by solid-phase extraction using a Sep-Pak Light C-18 cartridge. The procedure used for ketorolac extraction was as follows. Initially, the cartridge was conditioned with 2 ml of methanol followed by 3 ml of water and then 2 ml of phosphoric acid solution (1.3 mM) at pH 2.75. then 200 $\mu$l of serum sample, 100 $\mu$l of internal standard (tolmetin sodium 5 $\mu$g/ml in water) and 400 $\mu$l of water was loaded into each cartridge. The cartridges were successfully eluted with 1 ml of above phosphoric acid and 2 ml of water in order to remove unwanted components. Finally 2 ml of methanol was used to flush the ketorolac out of the cartridges. The methanolic extract was evaporated under a stream of nitrogen and the residue was redissolved in 200 $\mu$l of mobile phase (CH3CN/phosphoric acid (1.3 mM) 34:66, v/v) at pH 2.95.

For the preparation of the calibration curve, the same procedure as above was followed in order to develop a simulated environment. The cartridges were loaded with 200 $\mu$l of commercially processed rabbit serum, 100 $\mu$l internal standard (5 $\mu$g/ml), 100 $\mu$l Ketorolac tromethamine aqueous solution (1 $\mu$g/ml, 5 $\mu$g/ml, 8 $\mu$g/ml, 10 $\mu$g/ml and 20 $\mu$g/ml) and 300 $\mu$g/ml of water.

A Waters HPLC (Waters Associates, Milford, Mass.) equipped with an automated gradient controllers, Model 717 plus autosampler, Model 515 HPLC pumps, Model 480 LC spectrophotometer and Model 746 data module integrator was used. For chromatography, a $\mu$Bondapak C-18 column (3.9 mm i.d×30 cm, 10 Mm, Waters Associates) was used. The column was operated at ambient temperature. The mobile phase was made up of CH3CN/phosphoric acid (1.3 mM) 34:66, v/v) at pH 2.95. The absorption wavelength was set at 320 nm and injection volume of 20 $\mu$l was used.

A non-compartmental model analysis was employed to estimate the pharmacokinetic parameters of ketorolac tromethamine in serum. For data collected after a single dose, the terminal rate constant, half-life (t½), total area under the serum concentration time curve (AUC), maximum serum concentration (Cmax) and time to maximum concentration (Tmax) were determined.

The terminal rate constant was determined by log-linear regression of the terminal time points of the serum concentration-time curve (selected by inspection of a log-linear plot) and used to estimate terminal half-life. Areas under the serum concentration-time curve (AUCX) up to the late time point ("x") were calculated using the trapezoidal rule and were extrapolated to infinity using the ratio of ketorolac concentration at the last time point and terminal rate constant. The plasma concentration was normalized for both the dose and weight of the rabbits. The absolute bioavailability of nasal formulation was finally calculated by dividing the normalized AUC for the nasal formulation by the normalized AUC for i.v. formulation.

The blood profile data after 2 mg/kg i.v. injection of ketorolac tromethamine solution to rabbits was summarized in FIG. 1. It can be seen that i.v. formulation resulted in a high initial concentration of drug followed by an immediate decrease in drug concentration for 30 minutes and then the concentration was gradually decreased over a five hour period. The normalized area under the curve by both dose and weight was found to be an average of 1.00±0.159 (hr. $\mu$g/ml).

Control Nasal Aqueous Solution

Figure 2:
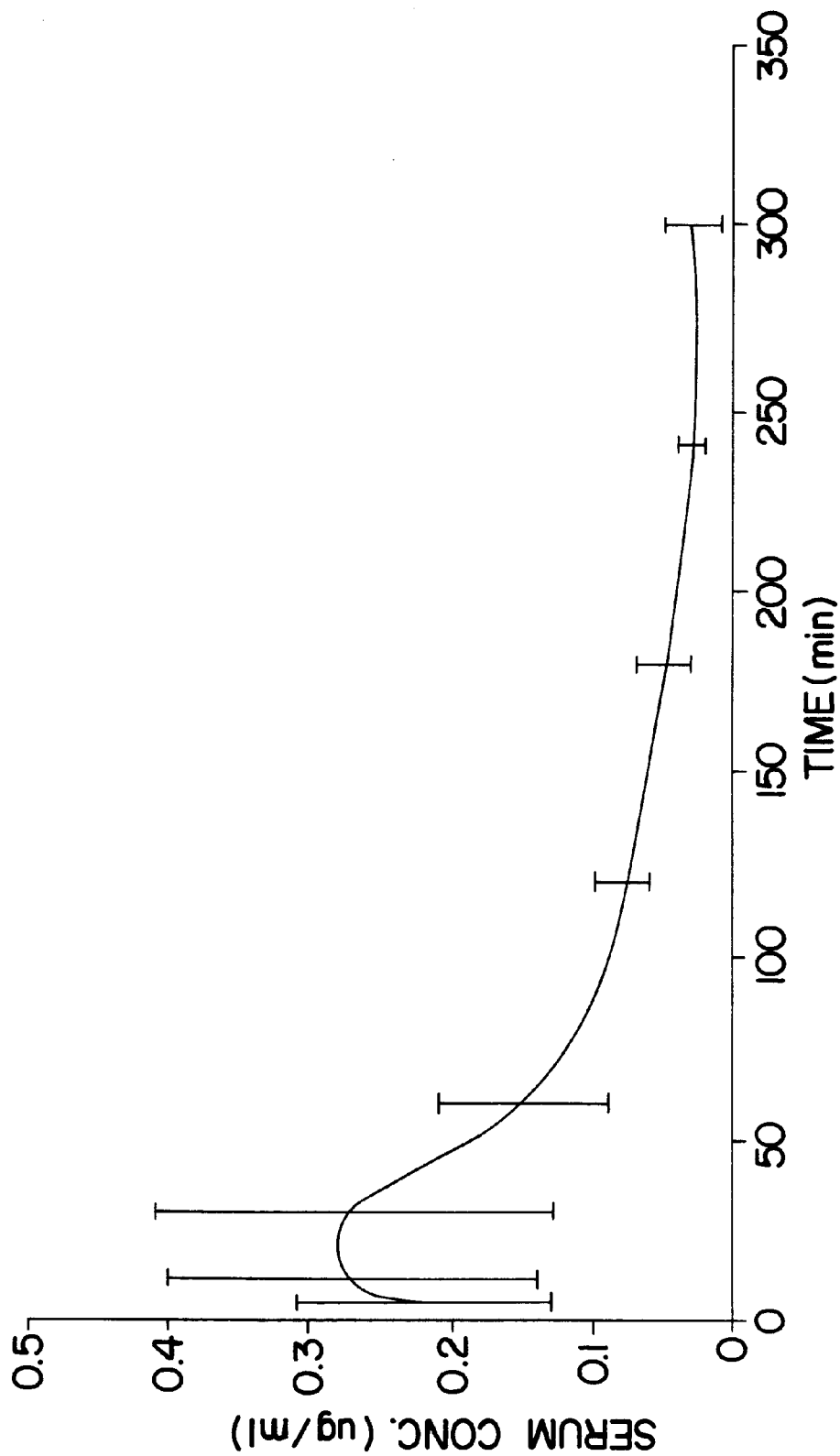
FIG. 2 shows the blood profile of ketorolac following an intranasal spray administration of drug (10 mg/200 µL of an aqueous solution) in rabbits.

When 100 $\mu$l of a 50 mg/ml of the control aqueous solution of the drug was sprayed into each nostril, there was a significant intra subject variation in the results of blood profile as is evidenced by extended Y-bars in FIG. 2. The normalized area under the curve was 0.59±0.106 (hr. $\mu$g/ml) which yielded an absolute bioavailability of 55%. The low bioavailability of this simple aqueous solution is mainly due to drainage of the sample solution caused by mucociliary clearance mechanism of the cilia which cover the nasal membrane, thus not giving sufficient time for the drug molecule to be absorbed.

According to the present invention we have overcome these two main difficulties by the addition of pharmaceutically acceptable carrier (microcrystalline cellulose) and use of a preservative such as 2-phenyethanol and/or benzyl alcohol.

Nasal Polymeric Formulation

Figure 3:
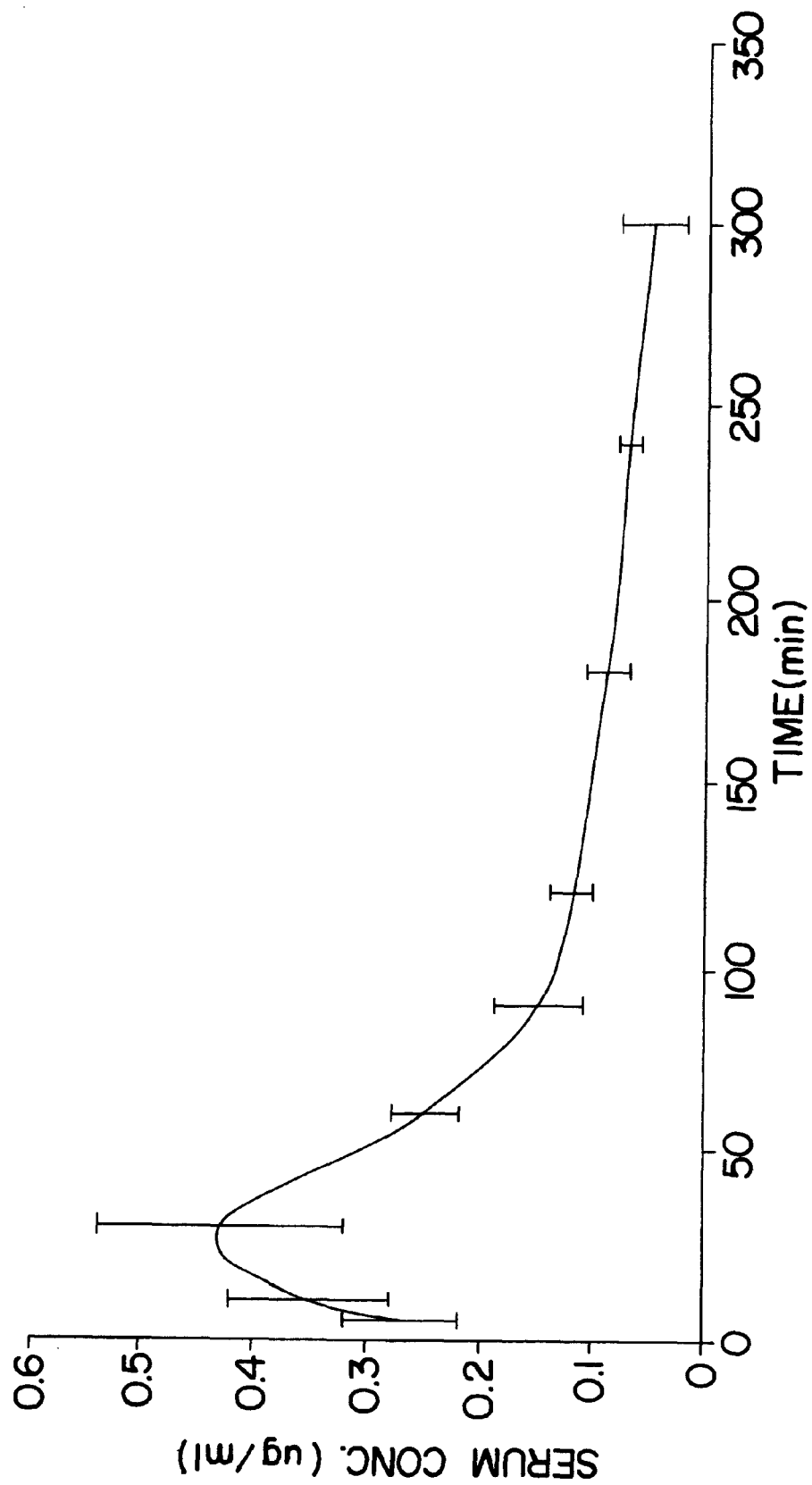
FIG. 3 shows the blood profile of ketorolac following an intranasal spray administration of drug (10 mg/200 µL of a polymeric aqueous solution) in rabbits.

When 100 $\mu$l of 50 mg/ml of ketorolac tromethamine polymeric formulation was sprayed into each nostril, there was a significant improvement in the bioavailability of the drug with a considerable decrease in variability of the data. The results obtained after dosing of nasal polymeric spray formulation is shown in FIG. 3. It can be seen from this figure that the nasal polymeric spray formulation has an increased concentration of ketorolac at approximately 5 minutes after dosing as compared to that of control aqueous solution. The average maximum serum concentration is 0.428±0.122 $\mu$g/ml occurring approximately 30 minutes after administration. The normalized area under the curve is 0.91±0.223 (hr. µg/ml) which indicates an absolute bioavailability of 91%.

The serum concentration after 3 hours is higher in case of the nasal polymeric formulation than in i.v. injection, which may indicate a longer period of drug action. It is believed that ketorolac tromethamine forms a complex with microcrystalline cellulose and/or adsorbs to this bioadhesive polymer so that the polymeric nasal formulation provides prolonged drug absorption which in turn gives an excellent bioavailability.

FIG. 4 shows the comparative bioavailability of the formulations studied. As is evident from this figure, the nasal polymeric formulation provide an in vivo bioavailability which is comparable to i.v. injection and therefor, such nasal formulation could easily by substituted for its injections, if the histological studies of the formulation proved to be safe.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A pharmaceutical nasal spray consisting of:

an effective amount of ketorolac based analgesic admixed with a phospholipid or a bioadhesive polymer selected from the group consisting of polyacrylics, cellulosics, gums, cyclodextrins, chitosans, hyaluronates and albumins said spray when administered intranasally having a therapeutic blood level compared to that of the same spray when injected.

2. The pharmaceutical nasal spray of claim 1 wherein the ketorolac based analgesic is ketorolac tromethamine.

3. The pharmaceutical nasal spray of claim 1 wherein the analgesic is present in the composition in an amount of between 2 to 15% by weight based on total weight of the composition.

4. The pharmaceutical nasal spray of claim 1 wherein the bioadhesive polymer is a cellulosic polymer.

* * * * *